(12) United States Patent
Silver

(10) Patent No.: US 8,747,349 B2
(45) Date of Patent: Jun. 10, 2014

(54) SOFT BREASTSHIELD

(75) Inventor: Brian H. Silver, Cary, IL (US)

(73) Assignee: Medela Holding AG (CH)

( * ) Notice: Subject to any disclaimer, the term of this patent is extended or adjusted under 35 U.S.C. 154(b) by 166 days.

(21) Appl. No.: 13/341,133

(22) Filed: Dec. 30, 2011

(65) Prior Publication Data

US 2012/0101432 A1 Apr. 26, 2012

Related U.S. Application Data

(63) Continuation of application No. 11/096,278, filed on Mar. 31, 2005, now Pat. No. 8,152,754.

(60) Provisional application No. 60/558,702, filed on Apr. 1, 2004.

(51) Int. Cl.
*A61M 1/06* (2006.01)

(52) U.S. Cl.
USPC ........................................................... 604/74

(58) Field of Classification Search
USPC .................................................. 604/74, 131
See application file for complete search history.

(56) References Cited

U.S. PATENT DOCUMENTS

| | | | |
|---|---|---|---|
| 4,249,481 A | 2/1981 | Adams | |
| 4,387,705 A | 6/1983 | Finney | |
| 4,501,585 A | 2/1985 | Friedman | |
| 4,772,262 A | 9/1988 | Grant et al. | |
| 4,799,922 A | 1/1989 | Beer et al. | |
| 5,049,126 A | 9/1991 | Larsson | |
| 5,542,921 A | 8/1996 | Meyers et al. | |
| 5,885,246 A | 3/1999 | Ford | |
| 6,110,141 A | 8/2000 | Nuesch | |
| 6,517,513 B1 | 2/2003 | Covington | |
| 6,547,756 B1 | 4/2003 | Greter et al. | |
| 6,663,587 B2 * | 12/2003 | Silver et al. | 604/74 |
| 6,676,631 B1 | 1/2004 | Greter | |
| 6,809,143 B2 | 10/2004 | Nowak et al. | |
| 8,152,754 B2 * | 4/2012 | Silver | 604/74 |
| 2002/0004642 A1 | 1/2002 | Cloud | |

FOREIGN PATENT DOCUMENTS

| | | |
|---|---|---|
| CN | 2409975 Y | 12/2000 |
| EP | 1 034 807 A | 9/2000 |
| EP | 1 735 031 | 10/2005 |
| GB | 2 138 686 A | 10/1984 |
| JP | 2002/11076 | 1/2002 |
| JP | 2003/205018 | 7/2003 |
| WO | WO8808312 A | 11/1988 |
| WO | WO0033897 | 6/2000 |
| WO | WO03105616 | 12/2003 |

OTHER PUBLICATIONS

European Search Report issued Feb. 22, 2008.
European Search Report and Opinion, EP Patent Application No. 100003971, Mailed Jul. 20, 2010.

* cited by examiner

*Primary Examiner* — Manuel Mendez
(74) *Attorney, Agent, or Firm* — McDonnell Boehnen Hulbert & Berghoff LLP

(57) ABSTRACT

A breastshield is constructed of a low Durometer material. The breastshield includes a nipple tunnel that generally accommodates the shape of a nipple and an aperture that conveys fluids through the breastshield.

16 Claims, 3 Drawing Sheets

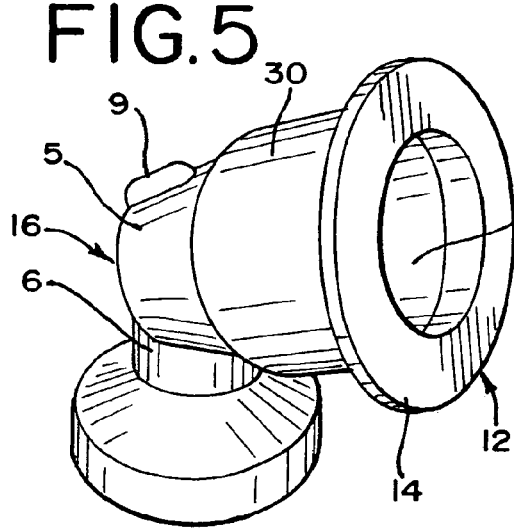
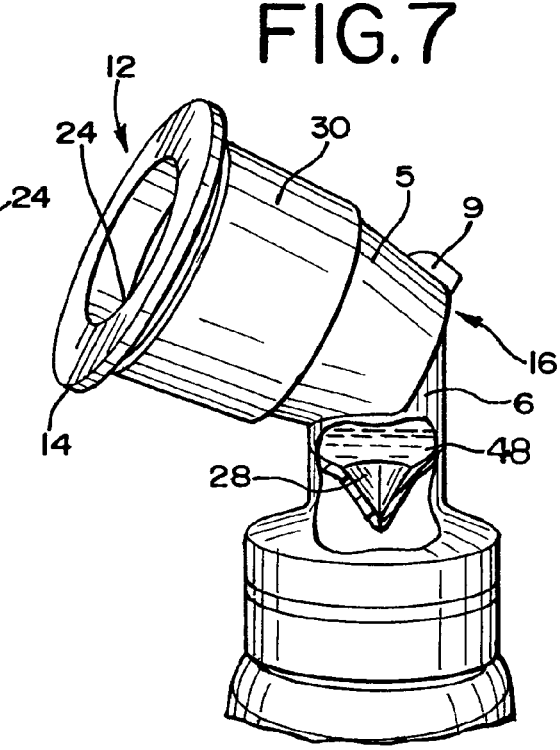
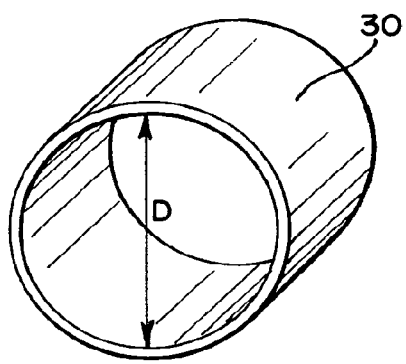
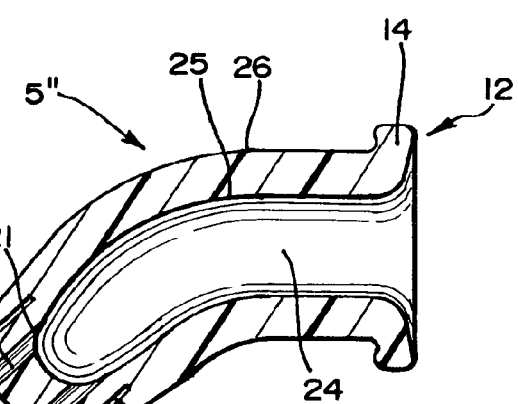
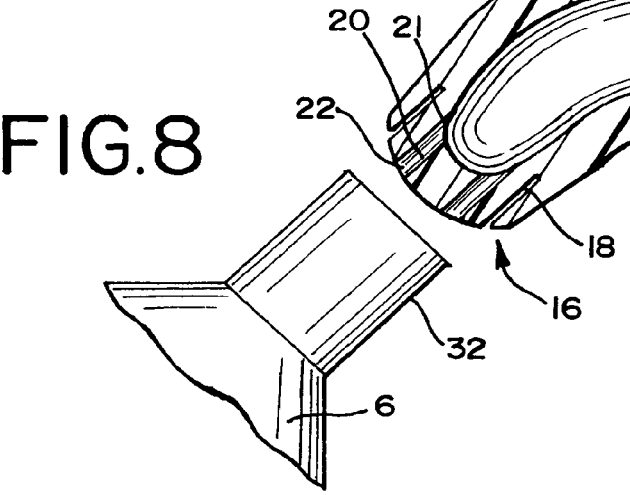

SOFT BREASTSHIELD

This application is a continuation of U.S. Ser. No. 11/096,278, filed Mar. 31, 2005, which claims priority to U.S. Provisional Application No. 60/558,702 filed Apr. 1, 2004. The entirety of the disclosure of the foregoing applications are hereby incorporated by reference, as if fully set forth herein.

FIELD OF THE INVENTION

The present invention relates generally to breastmilk pumps, and more particularly to breastshields used with breastpumps by nursing mothers.

BACKGROUND OF THE INVENTION

Breastpumps are well known, and generally are comprised of breastshields (also referred to as hoods) that fit over a portion of the breast including the nipple, a vacuum pump connected to the breastshield for generating an intermittent vacuum (negative pressure) within the breastshield, and typically a receptacle for the expressed milk. In its simplest and most common form, an intermittent suction action of the vacuum pump serves to pull on the breast and massage it so as to extract milk. The expressed milk typically drains from the shield into a collection container, such as a baby bottle, which is ordinarily attached directly to the breastshield apparatus, but can also be remote (with a tubular conduit connection). For breastpumps, manually driven vacuum pumps are commonplace, as well as those that are driven by a motor (house current, battery, pneumatic, etc). The present invention is not restricted to any kind of pumping mechanism.

The vacuum pumps intermittently generate a vacuum (or sometimes a positive pressure to compress a portion) within the breastshield, with the breastshield covering the nipple and typically an adjacent amount of the breast itself. The intermittent action of the pump serves to pull on (via vacuum) and compress the breast, and thereby extract milk in an action similar to suckling. The milk so expressed ordinarily flows from the breastshield into a collection container, e.g., a bottle, for storage and later use. A breastpump of the foregoing description is shown in U.S. Pat. Nos. 4,857,051, and 4,929,229, and reference thereto may be made for further detail on breastpumps in general.

Perhaps the most commonplace breastshields typically used in conjunction with breastpumps have a conical configuration and are usually funnel-shaped. These breastshields have traditionally been made using a regular truncated partial cone portion and a nipple tunnel extension at the downstream end of the cone portion. The nipple and surrounding breast are received in the cone portion, with the nipple extending into the nipple tunnel. Under vacuum, the breast is pulled further into the breastshield, ordinarily with the nipple then being pulled further into the nipple tunnel, with the surrounding breast thereby also compressed about the nipple.

A nursing mother's nipples may thus be forced against the wall of the nipple tunnel under vacuum. This may cause friction against the wall as the nipple moves deeper into the nipple tunnel. There can also be friction between the breast and the conical portion, as well as the nipple tunnel. The rigid structure against which the mother's breast is pressed is plainly not reminiscent of the soft mouth and palate of a baby.

Inserts for use within the hood or shield of a rigid breastshield assembly are also known, and have been used for sizing the breastshield. That is, an insert would be used in a larger funnel-shaped breastshield to reduce the internal diameter of the cone portion and/or nipple tunnel, for a smaller breast. Some rigid-type breastshields have also sometimes been employed with a flexible breast-engaging portion or device mounted interior of a rigid external support or frame, not so much as a sizing mechanism but in an attempt at improved milk expression as well as comfort.

SUMMARY OF THE INVENTION

A principal objective of the present invention is to provide an improved breastshield (or hood) for a breastpump, which in one significant aspect is very soft and pliant in the area of the nipple, and whatever surrounding breast may be further encompassed. An embodiment achieving the foregoing objective is substantially made of a low durometer material in all of the breast-engaging areas. That embodiment in a particularly desirable form is a generally solid piece of the low durometer material. In this desirable form, the breastshield is very soft and pliant, much like the baby's mouth and palate. It furthermore advantageously adapts to a wide variety of breast sizes ("one size fits all"), inasmuch as the orifice (opening) within which the nipple and breast is received has the ability to compress under pressure (negative and/or positive) in light of the very soft material. No internal adapters are therefore necessitated in this form. Furthermore, it will be understood that the breastshield of the present invention is used without any additional structure in the breast and nipple-contacting portion. In other words, unlike many prior art breastshields, which may include both a rigid shell and a relatively pliable liner or insert or bladder portion, the present invention operates without any outer shell or rigid elements or attached supporting elements supporting the main shield portion. The present breastshield functions without any need of rigid or outer shell elements.

In a particular aspect of the foregoing invention, the breastshield may be a Shore A hardness of about 20 or less than 20. The breastshield may be a Shore A hardness of about 10 or less than 10, and even at or below 1. More particularly, on the Shore 00 scale, a range of about 20 to about 45 is presently considered most desirable. One of the most significant attributes of the present invention is considered to be the very low durometer material of the breastshield, and how that material behaves under application of negative pressure thereto. The low durometer material is thought to minimize friction between the breast and breastshield in use. As will be evident herein, the most preferred durometers are considered to be in the range at or below Shore A 5, and most preferable Shore 00 of about 20 to about 45. Values below the noted range may have useful applications in the breastshield of the present invention.

Where the natural adaptability of the soft breastshield material alone may not suffice, another aspect of the invention is to provide a compression ring or rings for use with the breastshield, each of which is positioned around the outside of the breastshield in the area of the nipple tunnel, to vary the inside diameter of the nipple tunnel. In one such embodiment, adaptor rings are provided in a variety of differing internal diameters. The user chooses the ring that compresses the nipple tunnel material to the size she desires, with the chosen ring simply mounted around the nipple tunnel to compress it to size; or for that matter, shape, if a different shape for the tunnel is desired, which the ring system could readily accommodate. Thus, the separate rings may include a variety of sizes (diameters) and even shapes for selection of comfort. The compression ring may be constructed of a rigid material, for example a hard plastic, or an elastic band that causes the desired compression, a ratcheted belt, and so forth.

Other means for providing a variable inside diameter of the nipple tunnel are contemplated. For example, an inflatable or adjustable bladder or area of weakened material may be provided adjacent the nipple tunnel area of the present breastshield and provided with a fluid source which when pressurized, with either a negative or positive pressure may function to cause a variance in the diameter of the nipple tunnel. It will be understood that the illustrations provided herein are not limiting in nature.

The breastshield of this invention may be a separate piece that is mountable to a part of the breastpump (e.g., a mounting collar extending from a base structure or housing or conduit portion that attaches to a bottle), or made integral with adjacent parts of the breastpump (such as the foregoing base structure). In the latter respect, another aspect of the invention is to provide a breastshield integrated with the part of the breastpump that attaches to the collecting chamber (e.g., bottle), and which may further include an integrated valve structure.

One form of this inventive integrated breastshield comprises a two durometer feature: the foregoing low durometer material for the breastshield portion, and a relatively higher durometer material for the base structure including the collecting (or catch) chamber portion which itself attaches to the bottle mouth. The collecting chamber portion is an area where milk flows from the nipple tunnel and may momentarily reside before being passed to the container. The base structure is made (e.g., by molding) with a collar or mounting portion having a mating attachment adapted for the container mouth in point. This could be a threaded fit, snap-fit, and so on. In this dual-durometer form, all of the breastpump (sans container and vacuum source) can be formed in an integral piece. That could further include an integral valving structure at the downstream end of the collecting chamber. For instance, one embodiment contemplates a duckbill type valve molded of the same higher durometer material, which closes under vacuum but then allows milk to pass when the pressure is released.

Still another aspect of an embodiment of the invention is to provide a flexible breastshield that is curved or curvable, in whole or in part, for comfort. Typically, breastpumps are designed for use with the mother in a generally erect posture. The breastshield is thus angled upwardly relative to the collection container, the latter being generally vertical in this configuration. The nursing mother may wish to recline somewhat, or sit back for instance. The standard breastpump is not typically well adapted to accommodate this back-leaning posture, however, since the extracted milk must first essentially flow "up hill" into the funnel. Providing a breastshield with a curved body facilitates comfortably sitting back while still maintaining a "down hill" milk flow to the collection container. That curved body can be provided in the present invention through an elongated tunnel of the soft (low durometer) breastshield which may in part be curved, but which can be further curved simply through bending of the flexible breastshield into position by the mother to adapt the breastshield to the needed angle.

The present invention will be further appreciated, and its attributes and advantages further understood, with reference to the detailed description below of examples of presently contemplated embodiments, taken in conjunction with the accompanying drawings, in which:

BRIEF DESCRIPTION OF THE DRAWINGS

FIG. 5 is a perspective view of the breastshield and related integral base structure of FIG. 1;

FIG. 6 is a perspective view of a compression ring shown in FIGS. 1 and 5;

FIG. 7 is an elevational view, partly broken away, to show a valving device;

FIG. 8 is a modified version of the breastshield of FIGS. 2 through 4; and

DETAILED DESCRIPTION OF EMBODIMENTS OF THE INVENTION

The first embodiment discussed herein is a so-called dual-Durometer version, which is also depicted in FIGS. 1, 5, 7 and 9. As will be discussed in more detail below, this version has a very soft low Durometer part that makes up the breastshield proper, and a more rigid higher Durometer part that it is molded to the breastshield proper which makes up the rest of the breastpump, (exclusive of the container which is to receive the milk and the vacuum source).

Figure 1:
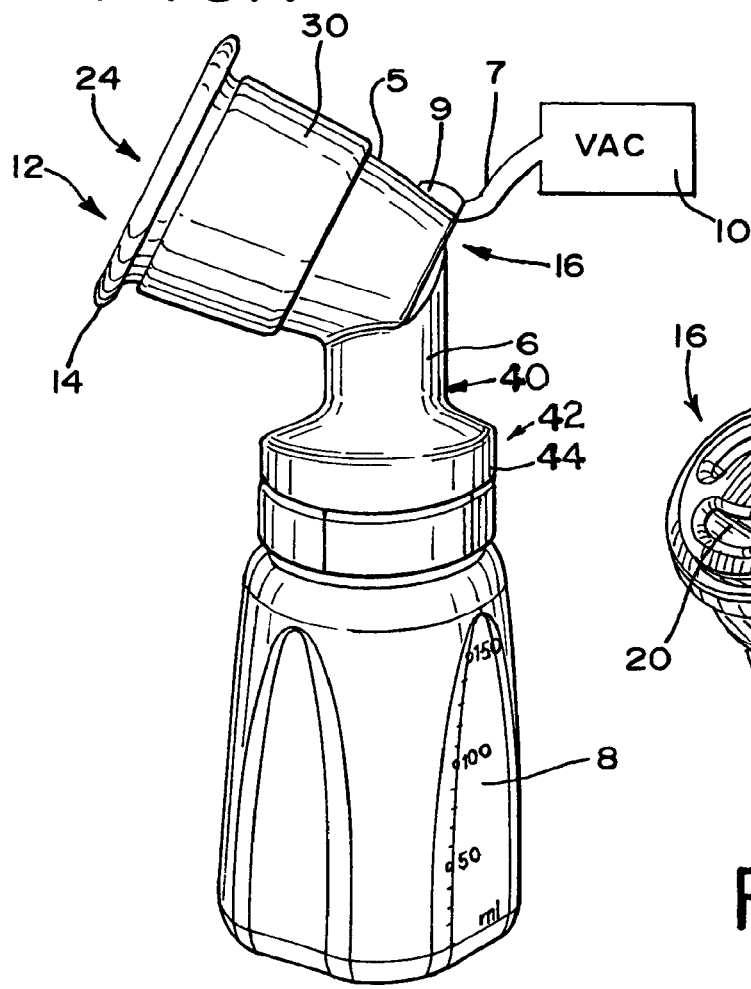
FIG. 1 is an elevational view of an assembled breastshield and related integrally formed base structure, with a collection container, made in accordance with certain aspects of the invention.

As shown in FIG. 1, the breastshield 5 connects to a base structure 40 that includes a liquid conduit (not shown, but interior to base 40), with a collecting or catch chamber 6, and a downstream end 42 having an attachment part 44 for mounting to a collection device (here, a bottle 8). Referring to FIG. 7, at the outlet of the collecting chamber 6 there may be provided a valve 28, which closes a passage (not shown), which is part of the liquid conduit, leading from the collecting chamber 6 to bottle 8. Valve 28 in this instance is known as a duckbill valve (FIG. 7). When a vacuum or negative pressure is applied to the breastshield 5 from a well-known type of suction device 10, which may be manually operated or motor driven, the valve 28 closes the collecting chamber outlet 48, and a negative pressure is applied to the interior of the breastshield 5. The outlet 48 is opened when the negative pressure is released, and the valve 28 opens to pass milk expressed into the breastshield and thence to the collecting chamber 6, to flow into the bottle 8. The valve mechanism may be of many other types, but as discussed further below, the duckbill type is considered most applicable in the context of this integrally molded dual-Durometer device.

The vacuum or suction device 10 may be a manually operated piston pump, a battery operated diaphragm pump, a house-current driven vacuum pump using a vacuum line (tube), among others. Again, reference can be made to U.S. Pat. Nos. 4,857,051, and 4,929,229, to glean details of the operation of pumps that may be used with the present invention. The invention herein is, however, not limited to any particular kind of vacuum device, or positive pressure device, for that matter. The vacuum source 10 connects via a tube 7 to a port 9 formed on the breastshield/base structure. The port 9 communicates with the interior 56 (see FIG. 4) of the breastshield 5.

The breastshield 5 may be made of any suitable soft, i.e., low Durometer, material, but in a preferred form is made of a soft silicone material, such as silicone rubber. It could alternatively be other materials, such as thermoplastic elastomers (TPE's).

It is most desirable is to have the material of which the breastshield 5 is fabricated with a Durometer A (or Shore A)

hardness that is substantially within the range of about 1 to about 20. More favorably, the material has a Durometer A hardness that is within the range of about 1 to about 5, or switching to the Shore 00 scale, most favorably in the range of about 20 to about 45. Below this range is nonetheless also considered efficacious.

The breastshield 5 has a wall thickness from about ⅛ inches to about ½ inches. In a more preferred form, the wall thickness is about ⅜ inches.

The Durometer of the rest of the base structure 40 is of a hardness that provides sufficient rigidity to facilitate attachment to the mouth of a container in a manner that will mount the breastshield in a stable configuration and resist application of a vacuum or positive pressure thereto.

Details of the manner in which a dual-Durometer structure of this kind can be made, and further particulars of the preferred ranges for the various Durometer considered most efficacious, can be gleaned from the co-pending application U.S. Ser. No. 10/696,910, which discloses such a dual-Durometer construction in the context of a feeding nipple. The novel construction in that application readily translates into the present application for a breastshield.

The breastshield 5 includes a collecting chamber portion 6, which is designed to be attachable to a container 8 in a fluid-tight manner. Alternatively, a secondary collar or like attachment piece could be used to attach the breastshield to the container. The material of which the collecting chamber portion 6 is fabricated preferably has a Durometer A hardness that may be formed of the same or a greater Durometer hardness than breastshield portion 5. In one embodiment, the collecting chamber portion 6 has a Durometer A hardness that is within the range of about 1 to about 100. More preferably, the material of the collecting chamber portion 6 has a Durometer A hardness that is substantially within the range of about 20 to about 90, or even more preferably in the range of about 70 to about 90. It will be understood that the collecting chamber portion 6 should have Durometer A hardness sufficient to enable secure and leak-free attachment to a container. The means for attachment to a container 8 include, for example, screw threads, a snap-fit, etc.

A compression ring 30 surrounds the outside of the breastshield 5. Because of the very soft and pliant material of the breastshield 5, it can be readily compressed to thereby change the size of the tunnel 24 within which the nipple and adjacent breast are received. Of course, the breastshield alone may provide a sufficient amount of resiliency to form-to-fit without the need of any compressive device. Here, however, a ring 30 may be used for sizing. The ring is made of a rigid plastic, although its function could likewise be accomplished in many other ways. With reference to FIG. 6, it is contemplated that a plurality of rings 30 would be made available, each of differing internal diameter D. Alternatively, a single rigid ring could be used which is split and thereby made adjustable, with some appropriate fixation mechanism to lock the ring to the desired size. Ring 30 is slipped over the breastshield 5 into place.

Figure 2:
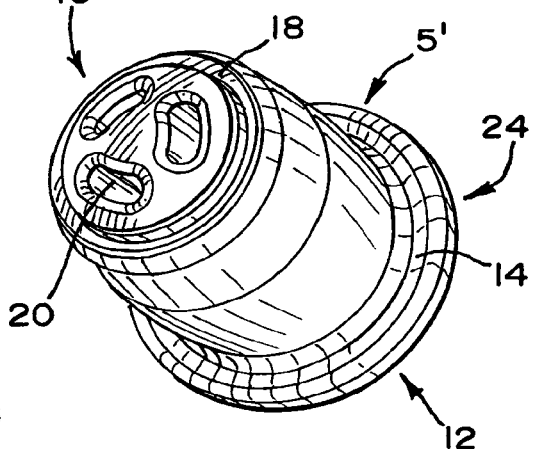
FIG. 2 is a perspective view of a breastshield made in accordance with this invention, as a separately mountable element.
Figure 3:
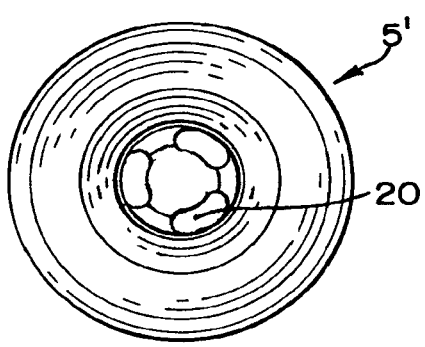
FIG. 3 is a front view of the breastshield of FIG. 2.

Turning now to FIG. 2, another embodiment of a breastshield made in accordance with the teachings of the present invention is shown. The breastshield is constructed of a low Durometer material. This embodiment is of a breastshield 5' which is separate from the rest of the breastpump, being adapted to be removably mounted thereon. The first end 12 of this embodiment 5' has a wide cross-section (diameter), and is generally circular in cross sectional shape (along its long axis), although any suitable cross-sectional shape is contemplated. The first end 12 further includes a circumferential flange or rim 14. A nipple tunnel 24 opens into the first end 12 and extends longitudinally towards the second and downstream end 16. During operation, the base of the circumferential rim 14 is placed over the breast of the user such that the nipple tunnel 24 resides over (surrounds) the nipple of the breast. Second end 16 of the breastshield 5 has a cross-section slightly narrower than the cross-section of the end 12.

The overall body of this breastshield 5' is generally cylindrical, although any shape of the overall body is contemplated. The second end 16 has a plurality of apertures 20. These apertures 20 allow for the passage of milk, as well as vacuum to and/or from the interior 56 of the breastshield 5'.

One arrangement of the plurality of apertures 20 is illustrated. The apertures 20 number three individual holes, although any suitable number of apertures is contemplated including one. The apertures 20 are "kidney bean" shaped, although any shape is contemplated, including trapezoidal. The apertures 20 are arranged in a circular pattern spaced outwardly from a middle or central axis of the breastshield 5'. Other arrangements of apertures 20 are contemplated that effectively convey fluids through the breastshield 5'; this is just one such.

Figure 4:
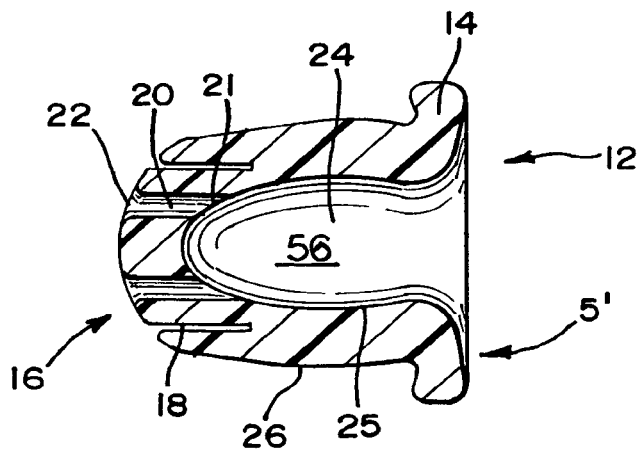
FIG. 4 is a sectional side view of the breastshield of FIG. 2.

As shown in FIG. 4, the apertures 20 are longitudinal (axial) passageways formed in the material of the breastshield 5'. Each aperture 20 includes an inner opening 21 in communication with the nipple tunnel 24. Each aperture 20 includes an outer opening 22 that is open to the exterior of the breastshield 5'. Fluid may flow from the nipple tunnel 24, into inner openings 21, though apertures 20 and out through outer openings 22 when negative pressure is applied. Negative fluid pressure likewise flows to and from the nipple tunnel 24 through the apertures 20.

Surrounding the apertures 20 is an annular gap 18 formed in the end 16. This gap serves to receive a complementary rigid ring-shaped collar 32 (see FIG. 8) therein, which thereby mounts the breastshield 5' to the rest of the base structure of the breastpump. The mounting structure of this kind of breastpump base is known in the art, but only with rigid breastshields, such as those that attach through an interference fit to collar 32.

The nipple tunnel 24 defines an inside diameter 25 and an outside diameter 26. The inside diameter 25 and outside diameter 26 further define a wall thickness of the breastshield 5. The wall thickness provides structure for the nipple tunnel 24 to hold its general shape.

FIG. 8 shows another embodiment of a breastshield 5", which is curved along its longitudinal length. Providing a breastshield with a curved body facilitates comfortably sitting back while allowing the collection container to remain relatively vertical. The curvature further facilitates even more bending of the breastshield 5" by the mother, if so desired, given the very soft and pliant nature of the breastshield 5" made of the same low Durometer material previously discussed.

Figure 9:
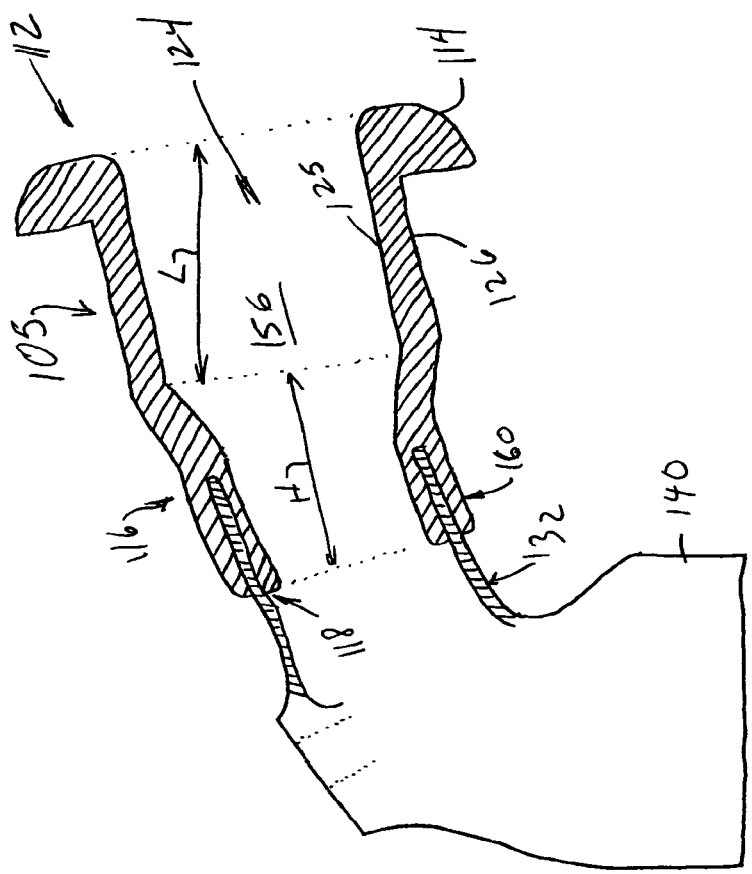
FIG. 9 is a sectional view of another embodiment of a breastshield according to the present invention.

FIG. 9 illustrates yet another embodiment of the breastshield 105 according to the present invention. Breastshield 105 includes a first end 112 sized and shaped to receive a nipple and at least a portion of the surrounding breast tissue of the mother. The first end 112 includes an annular radially extending flange or rim 114. The rim 114 has a wall thickness of about ⅜ inch, but it will be understood that a range of wall thickness are contemplated. The rim 114 defines a nipple tunnel 124 which leads into the interior 156 of breastshield 105 defined by inside surface 125. A first section "L" of the breastshield 105 is formed of the low Durometer material discussed previously and a second section "H" of the breastshield is formed of the relatively higher Durometer material discussed previously. The wall thickness of part 112 of this embodiment is about ¼ inch.

In this embodiment, the cross-section of section L is cylindrical. From first section L the breastshield 105 tapers or angles inwardly into section H which includes an attachment section 160 including an annular gap or groove 118 formed in the second or downstream end 116. The attachment section 160 receives collar 132 of base structure 140. The collar 132 is a cylindrical extension of the housing of the base structure 140.

Section H preferably may be made of a higher Durometer material than section L as detailed above to provide a secure attachment to both the softer silicone of section L and the base 140. Base 140 may be part of section H with increased rigidity or a separate part.

Thus, while a multitude of embodiments have been variously described herein, those of skill in this art will recognize that different embodiments show different potential features/designs that can be used in the other embodiments. Even more variations, applications and modifications will still fall within the spirit and scope of the invention, all as intended to come within the ambit and reach of the following claims.

What is claimed is:

1. A breastshield, comprising: a soft one-piece breastshield defining a nipple tunnel, said nipple tunnel having a changeable diameter, wherein said diameter of said nipple tunnel is configured to change in response to a compressive force applied to an outer surface of said breastshield in order to vary a size or a shape of said nipple tunnel without the aid of vacuum being applied to said breastshield.

2. The breastshield of claim 1, further including one or more sizing rings sized to fit over an outside surface of said breastshield, wherein one of said one or more sizing rings is coupled to said outside surface of said breastshield thereby compressing said changeable diameter of said nipple tunnel.

3. The breastshield of claim 2, wherein said one or more sizing rings is a plurality of sizing rings, each having a different internal diameter.

4. A breastshield, comprising: a soft one-piece breastshield defining a nipple tunnel, said nipple tunnel having a compressible diameter; and
    one or more compression rings sized to fit over an outside surface of said breastshield, wherein said one or more compression rings is configured to vary a size or a shape of said compressible diameter of said nipple tunnel, without the aid of vacuum being applied to said breastshield, when one of said one or more compression rings is coupled to said outside surface of said breastshield.

5. The breastshield of claim 4, wherein said one or more compression rings is a plurality of compression rings, each having a different internal diameter.

6. The breastshield of claim 4, wherein said one or more compression rings is a plurality of compression rings, each having a different shape.

7. The breastshield of claim 4, wherein said one or more compression rings defines an oval, cylindrical, frustoconical, or polygonal shape.

8. The breastshield of claim 4, wherein said one or more compression rings are constructed of a rigid material.

9. The breastshield of claim 4, wherein said one or more compression rings are made of a material with a greater durometer than that of said nipple tunnel.

10. The breastshield of claim 4, wherein said one or more compression rings is an elastic band.

11. The breastshield of claim 4, further comprising a fixation mechanism, wherein said one or more compression rings is a single compression ring, wherein said single compression ring defines an open channel such that said single compression ring has an adjustable diameter, and said fixation mechanism is coupled to the exterior of said single compression ring to compress said nipple tunnel to a desired size.

12. The breastshield of claim 11, wherein said fixation mechanism is one of an elastic band or a ratcheted belt.

13. A breastshield and sizing kit, comprising: a soft one-piece breastshield defining a nipple tunnel; and
    one or more sizing rings sized to fit over an outside surface of said breastshield, wherein said one or more sizing rings is a plurality of sizing rings, each having a different internal diameter configured to vary a size or a shape of said nipple tunnel to a variety of breast sizes, without the aid of vacuum being applied to said breastshield, when one of said plurality of sizing rings is coupled to said outside surface of said breastshield.

14. A breastshield, comprising: an elongated soft one-piece breastshield member having a nipple receptacle at one end of a nipple tunnel, said nipple tunnel extending along a longitudinal length of said breastshield member and wherein said breastshield member has a changeable diameter, wherein said diameter of said breastshield member is configured to change in response to a compressive force applied to an outside surface of said breastshield member in order to vary a size or a shape of the changeable diameter without the aid of vacuum being applied to said breastshield member.

15. The breastshield of claim 14, further including one or more sizing rings sized to fit over the outside surface of said nipple tunnel.

16. The breastshield of claim 15, wherein said one or more sizing rings is a plurality of sizing rings, each having a different internal diameter.

* * * * *